United States Patent [19]

Romer et al.

[11] Patent Number: 5,200,409
[45] Date of Patent: Apr. 6, 1993

[54] COMPOSITION AND USE OF SUBSTITUTED 1,3-DITHIOLO-AND 1,4-DITHIINOQUINOXALINES AS AN ANTIMICROBIAL

[75] Inventors: Duane R. Romer; Ravi B. Shankar; R. Garth Pews, all of Midland, Mich.

[73] Assignee: The Dow Chemical Company, Midland, Mich.

[21] Appl. No.: 887,036

[22] Filed: May 22, 1992

Related U.S. Application Data

[63] Continuation-in-part of Ser. No. 814,527, Dec. 30, 1991, abandoned.

[51] Int. Cl.$^5$ .................. C07D 495/04; A61K 31/459
[52] U.S. Cl. ...................................... 514/250; 544/345
[58] Field of Search ........................ 514/250; 544/345

[56] References Cited

U.S. PATENT DOCUMENTS

| | | | |
|---|---|---|---|
| 3,453,365 | 7/1969 | Lane et al. | 544/353 |
| 3,761,475 | 9/1973 | Kurihara et al. | 544/345 |
| 3,849,415 | 11/1974 | Kurihara et al. | 544/345 |
| 3,932,406 | 1/1976 | Buttner et al. | 424/250 |
| 4,038,393 | 7/1977 | Mixan et al. | 428/541 |
| 4,052,394 | 10/1977 | Mixan et al. | 544/345 |
| 4,075,204 | 2/1978 | Wilson et al. | 260/250 BC |
| 4,075,205 | 2/1978 | Wilson et al. | 544/345 |
| 4,172,133 | 10/1979 | Wilson et al. | 544/345 |
| 4,199,581 | 4/1980 | Mixan et al. | 544/345 |
| 4,210,645 | 7/1980 | Wilson et al. | 544/345 |
| 4,514,402 | 4/1985 | Brandes et al. | 514/250 |
| 4,960,886 | 10/1990 | Mukai et al. | 544/35 |

FOREIGN PATENT DOCUMENTS 66-13397  7/1966  Japan .

OTHER PUBLICATIONS

Saikachi Chemical Abstracts, 1962, vol. 57, Columns 16614f, "Compounds related to pyrazine. III. Synthesis of 2-Substituted Thiazolo($\beta$)quinoxaline", Saikachi et al., (Chem. Pharm. Bull. (Tokyo), 9,941–4 (1961)).
Chemical Abstracts, vol. 55, 26353g (Feb. 23, 1961), to Farbenfabriken Bayer Akt.—Ges.
Saikachi, Chemical Abstracts, vol. 59, 1634g (1962).
Derwent Publication, G6424, "Dihydrophenazine Fungicidal Compositions", Ihara Noyaku Co. Ltd. (JP13397/66, Aug. 24, 1964).
Derwent Publication, 89-290597/40, Ricoh KK, Feb. 24, 1988, (JO 1215-069-A).
Foye, W. O. et al., Journal of Pharmaceutical Sciences, vol. 64, No. 2, Feb. 1975, pp. 211–216, "Synthesis and Antimalarial Activity of Heterocyclic Alkyl Disulfides, Thiosulfates, and Dithio Acid Derivatives".

Primary Examiner—Mark L. Berch

[57] ABSTRACT

Substituted 1,3-dithiolo- and 1,4-dithiinoquinoxalines are prepared which correspond to the formula:

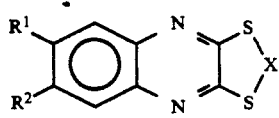

wherein X represents:

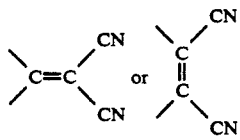

and $R^1$ and $R^2$ independently represent hydrogen, halogen, nitro, cyano, alkyl, alkoxy, arylcarbonyl, or an alkoxy carbonyl group.

These compounds have been found to exhibit antimicrobial and marine antifouling activity in industrial and commercial applications and compositions containing these compounds are so employed.

24 Claims, No Drawings

COMPOSITION AND USE OF SUBSTITUTED 1,3-DITHIOLO-AND 1,4-DITHIINOQUINOXALINES AS AN ANTIMICROBIAL

CROSS-REFERENCE TO RELATED APPLICATIONS

This application is a continuation-in-part of copending application Ser. No. 814,527, filed Dec. 30, 1991, abandoned.

BACKGROUND OF THE INVENTION

The field of this invention is novel substituted quinoxaline compounds which are useful as antimicrobial and marine antifouling agents.

Saikachi, H. and Tagami, S., *Yakugauku Zusshi*, 82, 1246–51 (1962), discloses the preparation of a compound of the formula:

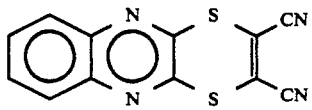

which is used as an intermediary in the preparation of a compound of the formula:

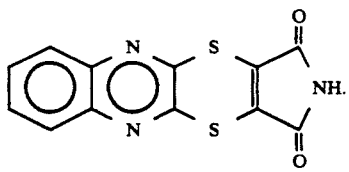

U.S. Pat. No. 3,761,475 discloses the preparation of a compound of the formula:

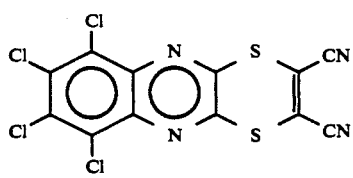

which is useful as a fungicide and bactericide.

JP-A-01215069 discloses a compound of the formula

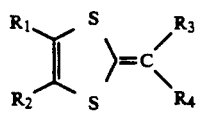

wherein $R_3$ and $R_4$ may be cyano and $R_1$ and $R_2$ may form a substituted heterocyclic aromatic ring. This compound is useful in a photoactive layer in a photoelectric conversion element.

JP-66/013397 discloses a compound of the formula:

which is useful in a fungicidal composition.

Foye, W. O. et al., *Journal of Pharmaceutical Sciences*, Vol. 64, No. 2, February 1975, pp. 211–216, "Synthesis and Antimalarial Activity of Heterocyclic Alkyl Disulfides, Thiosulfates, and Dithio Acid Derivatives", discloses the preparation of a compound of the formula:

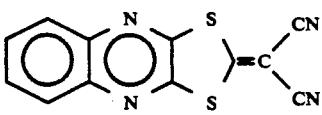

which is screened for antimalarial activity.

The desirability of identifying or discovering new antimicrobial and/or marine antifoulant agents is widely recognized. New agents are desired for several reasons: these include, but are not limited to, responding to the problem created by the development of microbe strains resistant to known agents, the occurrence of undesirable interactions of certain known agents with the medium or product in which the agent is used, and high toxicity of certain known agents to certain non-target organisms such as mammals.

The present invention solves these problems by disclosing new compounds which may be employed as an antimicrobial and/or a marine antifoulant agent.

SUMMARY OF THE INVENTION

The present invention is a compound corresponding to the formula:

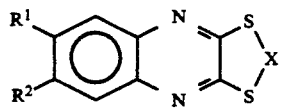

wherein X represents:

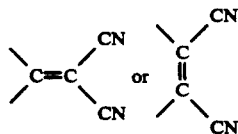

and $R^1$ and $R^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without substituents, provided that at least one of $R^1$ and $R^2$ is a nitro, cyano, alkoxy, arylcarbonyl, or an alkoxy carbonyl group.

The present invention is also an antimicrobial composition comprising an inert diluent and an antimicrobially-effective amount of a compound corresponding to the formula:

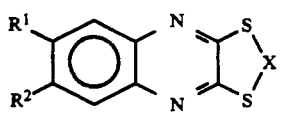

wherein X represents:

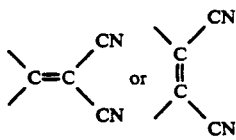

and R$^1$ and R$^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without substituents, provided that at least one of R$^1$ and R$^2$ is a nitro, cyano, alkoxy, arylcarbonyl, or an alkoxy carbonyl group.

The present invention is also a method for inhibiting microorganisms in a microbial habitat comprising contacting said microbial habitat with an antimicrobially-effective amount of a compound corresponding to the formula:

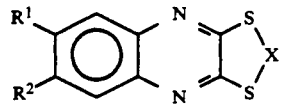

wherein X represents:

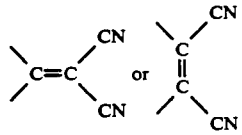

and R$^1$ and R$^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without substituents, provided that at least one of R$^1$ and R$^2$ is a nitro, cyano, alkoxy, arylcarbonyl, or an alkoxy carbonyl group.

The present invention is also a composition useful in preventing the growth of marine organisms on a surface exposed to a marine environment in which marine organisms grow comprising an inert diluent and a marine antifouling effective amount of a compound corresponding to the formula:

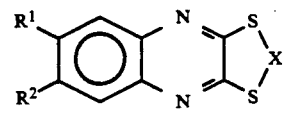

wherein X represents:

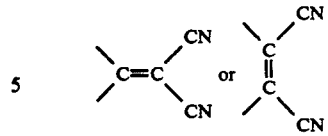

and R$^1$ and R$^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without substituents.

The present invention is also a method for preventing the growth of marine organisms on a surface exposed to a marine environment in which marine organisms grow comprising contacting said surface with a marine antifouling effective amount of a compound corresponding to the formula:

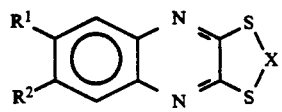

wherein X represents:

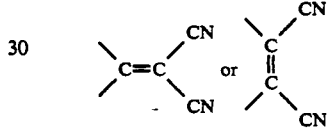

and R$^1$ and R$^2$ independently represent hydrogen, halogen nitro, cyano, alkyl, alkoxy, arylcarbonyl, or an alkoxy carbonyl group, wherein the alkyl, alkoxy, arylcarbonyl, or alkoxy carbonyl may be with or without substituents.

DETAILED DESCRIPTION OF THE INVENTION

The 1,3-dithiolo- and 1,4-dithiinoquinoxaline compounds of the present invention correspond to the formula:

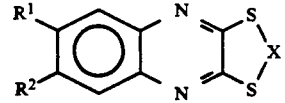

wherein X represents:

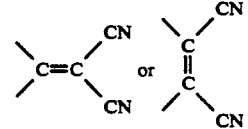

and R$^1$ and R$^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without substituents. Typically, it is preferred that at least one of R$^1$ and R$^2$ is a nitro, cyano, alkoxy, arylcarbonyl, or an alkoxy carbonyl group. In one embodiment of the present invention, it is preferred that R$^1$ and R$^2$ are not both halogen. Preferably, $R^1$ represents CN, $CO_2CH_3$, $OCH_3$, $COC_6H_5$, or $NO_2$ when $R^2$ represents H or $R^1$ represents H, Cl, $CH_3$ or $NO_2$ when $R^2$ represents $NO_2$. Most preferably, one or both of $R^1$ and $R^2$ represents $NO_2$.

In the present specification and claims, the term "halogen" is employed to designate fluorine, chlorine, bromine, iodine, or astatine. Preferably, halogen is employed to designate fluorine, chlorine, bromine, or iodine.

In the present specification and claims, the term "alkyl" is employed to designate straight chain and branched chain alkyls. Such alkyls may be with or without substituents, such as halogen. Preferably, the term "alkyl" is employed to designate straight chain alkyls of 1 to 6 carbon atoms and branched chain alkyls of 3 to 6 carbon atoms. Most preferably, the term "alkyl" is employed to designate straight chain alkyls of 1 to 4 carbon atoms, such as methyl, ethyl, propyl or butyl and branched chain alkyls of 3 to 4 carbon atoms, such as isopropyl or tertiary butyl.

In the present specification and claims, the term "alkoxy" is employed to designate a group of the formula:

$R^3$ represents an alkyl group, which may be with or without substituents, such as halogen. Preferably, the term "alkoxy" is employed to designate an alkoxy with an alkyl group of 1 to 6 carbon atoms. Most preferably, the term "alkoxy" is employed to designate an alkoxy with an alkyl group of 1 to 3 carbon atoms, such as methoxy or ethoxy.

In the present specification and claims, the term "arylcarbonyl" is employed to designate a group of the formula:

wherein $R^4$ represents an aryl group, which may be with or without substituents, such as halogen.

In the present specification and claims, the term "aryl" is employed to designate groups which have the ring structure characteristic of benzene, wherein the ring may be with or without substituents such as alkyl, cyclic alkyl, alkoxy, or halogen. The aryl ring may also be a fused ring, wherein the ring may have one or more of its sides in common with another ring. Preferably, the aryl ring has no more than three substituents. Most preferably, the aryl is phenyl.

In the present specification and claims, the term "alkoxy carbonyl" is employed to designate a group of the formula:

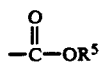

wherein $R^5$ represents an alkyl group, which may be with or without substituents, such as halogen. Preferably, the term "alkoxy carbonyl" is employed to designate an alkoxy carbonyl with an alkyl group of 1 to 6 carbon atoms. Most preferably, the term "alkoxy carbonyl" is employed to designate an alkyl carboxy ester with an alkyl group of 1 to 3 carbon atoms, such as methyl carboxy ester or ethyl carboxy ester.

Compounds of the present invention wherein X represents:

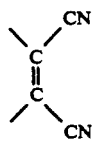

may be prepared by the reaction of an appropriately substituted 2,3-dichloro-6-quinoxaline precursor with disodium dimercaptomaleonitrile. The general reaction scheme for this reaction is as follows:

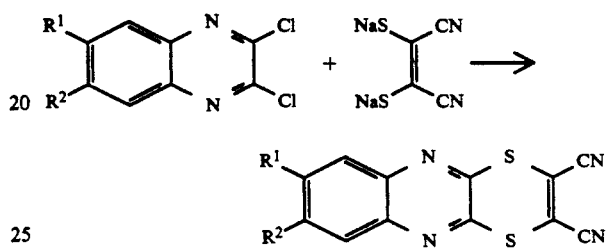

The use of disodium dimercaptomaleonitrile to prepare other compounds is known and and is generally disclosed in U.S. Pat. No. 3,761,475: U.S. Pat. No. 4,172,133: U.S. Pat. No. 4,199,581 and U.S. Pat. No. 4,210,645.

As used herein, the term "appropriately substituted 2,3-dichloro-6-quinoxaline precursor" is meant to refer to a compound of the formula:

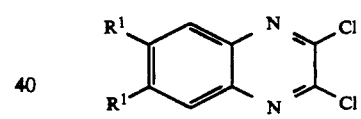

wherein $R^1$ and $R^2$ independently represent the hydrogen, halogen, nitro, cyano, alkyl, alkoxy, arylcarbonyl, or an alkoxy carbonyl group necessary to achieve the desired substituted 1,3-dithiolo- or 1,4-dithiinoquinoxaline final product.

Compounds of the present invention wherein X represents:

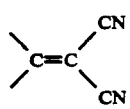

may be prepared by the reaction of an appropriately substituted 2,3-dichloro-6-quinoxaline precursor with di(sodiomercapto)methylenemalononitrile or di(potasiomercapto)methylenemalononitrile. The general reaction scheme for this reaction is as follows:

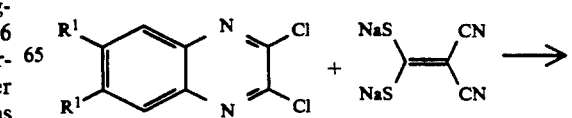

-continued

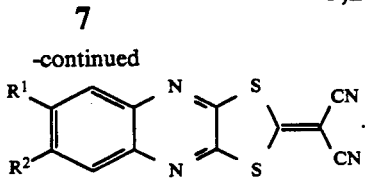

The use of di(sodiomercapto)methylenemalononitrile to prepare other compounds is known and is generally disclosed in U.S. Pat. No. 4,038,393: U.S. Pat. No. 4,075,204 and U.S. Pat. No. 4,075,205.

In carrying out these reactions, the appropriately substituted 2,3-dichloro-6-quinoxaline precursor and the di(sodiomercapto) or di(potassiomercapto)methylenemalononitrile and/or disodium dimercaptomaleonitrile are typically mixed together in substantially equimolar amounts. The reactions, however, are generally not limited to the use of the sodium salt of the dimercaptans. Typically, any suitable alkaline or alkali earth metal salt may be used such as, for example, the dipotassium salts of the dimercaptans.

The reactions are typically carried out at room temperature under an ambient pressure of an inert gas in the presence of a polar, aprotic solvent, such as dimethylformamide or dimethylsulfoxide. Typically, any order of addition of the reagents may be used and the reagents may be added neat or as a solution in the solvent used for the reaction. Subsequent to the addition of the appropriate reaction reagents, the reaction mixture will typically be allowed to continue at a temperature of between about 25° C. to about 60° C. over a period of about 1 to about 24 hours. The reaction product may typically be isolated by adding a 3 to 10 volume excess of water which will precipitate the desired product. Filtration followed by washing and drying yields the desired 1,3-dithiolo- and/or 1,4-dithiinoquinoxaline compounds of the present invention.

Synthesis of Intermediate Appropriately Substituted 2,3-Dichloro-6-Quinoxaline

The synthesis of the appropriately substituted 2,3-dichloro-6-quinoxaline precursor begins with the chlorination of an appropriately substituted 2,3-dihydroxyquinoxaline. This chlorination is straightforward and is described in the art, such as in Cheeseman, G. W. H., *J. Chem. Soc.*, 1962, p. 1170.

The following examples illustrate the present invention and the manner by which it can be practiced but, as such, should not be construed as limitations upon the overall scope of the same.

Preparation of
1,4-Dithiino-(2,3-b)quinoxalines-2,3-Dicarbonitriles

EXAMPLE 1

Preparation of
7-Nitro-1,4-dithiino(2,3-b)quinoxaline-2,3-dicarbonitrile

To a solution of 2,3-dichloro-6-nitroquinoxaline (1.0 g, 0.0041 mol) in dimethylformamide (20 mL) is added, in several portions, disodium-Z-1,2-dicyano-1,2-ethylenedithiolate (1.1 g, 0.0045 mol). The resulting solution is stirred overnight at room temperature. Water (100 mL) is slowly added to the reaction mixture, dropwise, with stirring. The resulting solid is isolated by filtration, washed with water and dried, giving a dark purple powder.

The recovered material weighs 0.92 g and has a melting point of 222° to 225° C. A calculated overall yield of 72 percent is achieved.

The structure identity is confirmed by proton nuclear magnetic resonance spectroscopy ($^1$H), carbon nuclear magnetic resonance spectroscopy (NMR), infrared spectroscopy (IR) and mass spectrometry (MS).

EXAMPLE 2

Preparation of
7,8-Dinitro-1,4-dithiino-(2,3-b)quinoxaline-2,3-dicarbonitrile

The process of Example 1 is followed except that the 2,3-dichloro-6-nitroquinoxaline is replaced by 1.25 g of 2,3-dichloro-6,7-dinitroquinoxaline and 0.966 g of the disodium-Z-1,2-dicyano-1,2-ethylenedithiolate is used. The recovered material is a reddish powder weighing 1.16 g with a calculated overall yield of 75 percent and has a melting point of 230° to 233° C.

EXAMPLE 3

Preparation of
7-Chloro-1,4-dithiino-(2,3-b)quinoxaline-2,3-dicarbonitrile

The process of Example 1 is followed except that the 2,3-dichloro-6-nitroquinoxaline is replaced by 3.00 g of 2,3,6-trichloroquinoxaline and 2.99 g of the disodium-Z-1,2-dicyano-1,2-ethylenedithiolate is used. The recovered material is a dark orange powder weighing 2.87 g with a calculated overall yield of 74 percent and has a melting point of 278° to 280° C.

EXAMPLE 4

Preparation of
7-Methyl-1,4-dithiino-(2,3-b)quinoxaline-2,3-dicarbonitrile

The process of Example 1 is followed except that the 2,3-dichloro-6-nitroquinoxaline is replaced by 3.0 g of 2,3-dichloro-6-methylquinoxaline and 3.3 g of the disodium-Z-1,2-dicyano-1,2-ethylenedithiolate is used. The recovered material is an orange powder weighing 3.52 g with a calculated overall yield of 88 percent and has a melting point of 213° to 215° C.

EXAMPLE 5

Preparation of
1,4-Dithiino-(2,3-b)-quinoxaline-2,3-dicarbonitrile

The process of Example 1 is followed except that the 2,3-dichloro-6-nitroquinoxaline is replaced by 4.0 g of 2,3-dichloroquinoxaline and 4.68 g of the disodium-Z-1,2-dicyano-1,2-ethylenedithiolate is used. The recovered material is a reddish powder weighing 4.58 g with a calculated overall yield of 85 percent and has a melting point of greater than 300° C.

EXAMPLE 6

Preparation of
7-Nitro-8-methyl-1,4-Dithiino-(2,3-b)-quinoxaline-2,3-dicarbonitrile The process of Example 1 is followed except that the 2,3-dichloro-6-nitroquinoxaline is replaced by 1.5 g of 2,3-dichloro-6-nitro-7-methylquinoxaline and 1.4 g of the disodium-Z-1,2-dicyano-1,2-ethylenedithiolate is used. The recovered material is a dark orange powder weighing 1.5 g with a calculated overall yield of 79 percent and has a melting point of 155° to 157° C.

EXAMPLE 7

Preparation of
7-Chloro-8-nitro-1,4-dithiino-(2,3-b)-quinoxaline-2,3-dicarbonitrile The process of Example 1 is followed except that the 2,3-dichloro-6-nitroquinoxaline is replaced by 1.0 g of 2,3-dichloro-6-chloro-7-nitroquinoxaline and 0.81 g of the disodium-Z-1,2-dicyano-1,2-ethylenedithiolate is used. The recovered material is an orange powder weighing 0.90 g with a calculated overall yield of 72 percent and has a melting point of 228° to 230° C.

EXAMPLE 8

Preparation of
7-Cyano-1,4-dithiino(2,3-b)-quinoxaline-2,3-dicarbonitrile

The process of Example 1 is followed except that the 2,3-dichloro-6-nitroquinoxaline is replaced by 0.33 g of 2,3-dichloro-6-cyanoquinoxaline and 0.39 g of the disodium-Z-1,2-dicyano-1,2-ethylenedithiolate is used. The recovered material is a yellow powder weighing 0.34 g with a calculated overall yield of 79 percent and has a melting point of 218° to 220° C.

EXAMPLE 9

Preparation of
7-Carbomethoxy-1,4-dithiino-(2,3-b)-quinoxaline-2,3-dicarbonitrile The process of Example 1 is followed except that the 2,3-dichloro-6-nitroquinoxaline is replaced by 0.55 g of 2,3-dichloro-6-carbomethoxyquinoxaline and 0.56 g of the disodium-Z-1,2-dicyano-1,2-ethylenedithiolate is used. The recovered material is a dark orange powder weighing 0.36 g with a calculated overall yield of 53 percent and has a melting point of 133° to 135° C.

EXAMPLE 10

Preparation of
7-Methoxy-1,4-dithiino-(2,3-b)-quinoxaline-2,3-dicarbonitrile

The process of Example 1 is followed except that the 2,3-dichloro-6-nitroquinoxaline is replaced by 0.75 g of 2,3-dichloro-6-methoxyquinoxaline and 0.76 g of the disodium-Z-1,2-dicyano-1,2-ethylenedithiolate is used. The recovered material is a dark orange powder weighing 0.81 g with a calculated overall yield of 82 percent and has a melting point of 154° to 156° C.

EXAMPLE 11

Preparation of
7-Trifluoromethyl-1,4-dithiino-(2,3-b)-quinoxaline-2,3-dicarbonitrile The process of Example 1 is followed except that the 2,3-dichloro-6-nitroquinoxaline is replaced by 0.50 g of 2,3-dichloro-6-trifluoromethylquinoxaline and 0.49 g of the disodium-Z-1,2-dicyano-1,2-ethylenedithiolate is used. The recovered material is an orange powder weighing 0.18 g with a calculated overall yield of 29 percent and has a melting point of 197° to 199° C.

EXAMPLE 30

Preparation of
7-Benzoyl-1,4-dithiino-(2,3-b)-quinoxaline-2,3-dicarbonitrile

The process of Example 1 is followed except that the 2,3-dichloro-6-nitroquinoxaline is replaced by 1.50 g of 2,3-dichloro-6-benzoylquinoxaline and 1.0 g of the disodium-Z-1,2-dicyano-1,2-ethylenedithiolate is used. The recovered material is a reddish-brown powder weighing 1.2 g with a calculated overall yield of 65 percent.

Preparation of
1,3-Dithiolo-(4,5-b)-quinoxaline-2-ylidene-propanedinitriles

EXAMPLE 12

Preparation of
6-Nitro-1,3-Dithiolo-(4,5-b)-quinoxaline-2-ylidene-propanedinitrile To a solution of 2,3-dichloro-6-nitro-quinoxaline (0.5 g, 0.002 mol) in dimethylformamide (15 mL) is added, in several portions, di(sodiomercapto)methylenemalononitrile (0.53 g, 0.0029 mol). The resulting solution is stirred overnight at room temperature. Water (50 mL) is slowly added to the reaction mixture, dropwise, with stirring. The resulting solid is isolated by filtration, washed with water and dried, giving 0.48 g (78 percent yield) of a dark brown powder.

EXAMPLE 13

Preparation of
6-Nitro-1,3-dithiolo-(4,5-b)-quinoxaline-2-ylidene-propanedinitrile The process of Example 12 is followed except that the di(sodiomercapto)methylenemalononitrile is replaced by di(potassiomercapto)methylenemalononitrile (0.63 g, 0.0029 mole). The recovered material is a dark brown powder, weighing 0.48 g with a calculated overall yield of 78 percent and has a melting point of 220° to 222° C.

EXAMPLE 14

Preparation of
6,7-Dinitro-1,3-dithiolo-(4,5-b)-quinoxaline-2-ylidene-propanedinitrile The process of Example 13 is followed except that the 2,3-dichloro-6-nitroquinoxaline is replaced by 1.25 g of 2,3-dichloro-6,7-dinitroquinoxaline and 1.13 g of the di(potassiomercapto)methylenemalononitrile is used. The recovered material is a dark brown powder weighing 1.26 g with a calculated overall yield of 82 percent and has a melting point greater than 300° C.

EXAMPLE 15

Preparation of
6-Methyl-1,3-dithiolo-(4,5-b)-quinoxaline-2-ylidene-propanedinitrile The process of Example 13 is followed except that the 2,3-dichloro-6-nitroquinoxaline is replaced by 3.0 g of 2,3-dichloro-6-methylquinoxaline and 3.84 g of the di(potassiomercapto)methylenemalononitrile is used. The recovered material is a yellow powder weighing 2.9 g with a calculated overall yield of 73 percent and has a melting point of 265° to 267° C.

EXAMPLE 16

Preparation of
6-Chloro-1,3-dithiolo-(4,5-b)-quinoxaline-2-ylidene-propanedinitrile The process of Example 13 is followed except that the 2,3-dichloro-6-nitroquinoxaline is replaced by 3.0 g of 2,3,6-trichloroquinoxaline and 3.5 g of the di(potassiomercapto)methylenemalononitrile is used. The recovered material is a dark brown powder weighing 3.0 g with a calculated yield of 78 percent and has a melting point greater than 300° C.

EXAMPLE 17

Preparation of
1,3-Dithiolo-(4,5-b)-quinoxaline-2-ylidene-propanedinitrile

The process of Example 13 is followed except that the 2,3-dichloro-6-nitroquinoxaline is replaced by 3.0 g of 2,3-dichloroquinoxaline and 3.95 g of the di(potassiomercapto)methylenemalononitrile is used. The recovered material is a light tan powder weighing 2.8 g with a calculated overall yield of 69 percent and has a melting point greater than 320° C.

EXAMPLE 18

Preparation of
6-Chloro-7-nitro-1,3-dithiolo-(4,5-b)-quinoxaline-2-ylidene-propanedinitrile The process of Example 13 is followed except that the 2,3-dichloro-6-nitroquinoxaline is replaced by 1.5 g of 2,3,6-trichloro-7-nitroquinoxaline and 1.4 g of the di(potassiomercapto)methylenemalononitrile is used. The recovered material is a rust colored powder weighing 1.23 g with a calculated overall yield of 66 percent and has a melting point of 297° to 299° C.

EXAMPLE 19

Preparation of
6-Nitro-7-methyl-1,3-dithiolo-(4,5-b)-quinoxaline-2-ylidene-propanedinitrile The process of Example 13 is followed except that the 2,3-dichloro-6-nitroquinoxaline is replaced by 1.5 g of 2,3-dichloro-6-nitro-7-methylquinoxaline and 1.5 g of the di(potassiomercapto)methylenemalononitrile is used. The recovered material is a dark yellow powder weighing 1.35 g with a calculated overall yield of 71 percent and has a melting point of 283° to 284° C.

EXAMPLE 20

Preparation of
6-Cyano-1,3-dithiolo-(4,5-b)-quinoxaline-2-ylidene-propanedinitrile The process of Example 13 is followed except that the 2,3-dichloro-6-nitroquinoxaline is replaced by 0.33 g of 2,3-dichloro-6-cyanoquinoxiline and 0.39 g of the di(potassiomercapto)methylenemalononitrile is used. The recovered material is a yellow powder weighing 0.33 g with a calculated overall yield of 76 percent and has a melting point of 278° to 281° C.

EXAMPLE 21

Preparation of
6-Trifluoromethyl-1,3-dithiolo-(4,5-b)-quinoxaline-2-ylidene-propanedinitrile The process of Example 13 is followed except that the 2,3-dichloro-6-nitroquinoxaline is replaced by 0.50 g of 2,3-dichloro-6-trifluoromethylquinoxaline and 0.49 g of the di(potassiomercapto)methylenemalononitrile is used. The recovered material is a dark yellow powder weighing 0.56 g with a calculated overall yield of 88 percent and has a melting point of 197° to 199° C.

EXAMPLE 22

Preparation of
6-Methoxy-1,3-dithiolo-(4,5-b)-quinoxaline-2-ylidene-propanedinitrile The process of Example 13 is followed except that the 2,3-dichloro-6-nitroquinoxaline is replaced by 0.75 g of 2,3-dichloro-6-methoxyquinoxaline and 0.90 g of the di(potassiomercapto)methylenemalononitrile is used. The recovered material is a dark yellow powder weighing 0.78 g with a calculated overall yield of 79 percent.

EXAMPLE 31

Preparation of
6-Benzoyl-1,3-dithiolo-(4,5-b)-quinoxaline-2-ylidene-propanedinitrile The process of Example 13 is followed except that the 2,3-dichloro-6-nitroquinoxaline is replaced by 1.5 g of 2,3-dichloro-6-benzoylquinoxaline and 1.2 g of the di(potassiomercapto)methylenemalononitrile is used. The recovered material is a reddish brown powder weighing 1.0 g with a calculated overall yield of 54 percent.

Antimicrobial Activity

The compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, not all of the compounds disclosed herein are active at the same concentrations or against the same microbial species. That is, there is some compound-to-compound variation in antimicrobial potency and spectrum of antimicrobial activity.

The present invention is also directed to a method for inhibiting microorganisms which comprises contacting said microorganisms or habitat thereof with an effective amount of the compound of this invention.

The antimicrobial compounds of this invention may be added directly to aqueous formulations susceptible to microbial growth, either undiluted or dissolved in inert diluents such as organic solvents such as glycols, alcohols, or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of two or more of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts vary depending upon the particular compound tested and mircoorganism treated. Also, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

TABLE I

| Compound No. | Chemical Identity |
|---|---|
| A | 7-nitro-1,4-dithiino-(2,3-b)-quinoxaline-2,3-dicarbonitrile |
| B | 7,8-dinitro-1,4-dithiino-2(2,3-b)-quinoxaline-2,3-dicarbonitrile |
| C | 7-chloro-1,4-dithiino-(2,3-b)-quinoxaline-2,3-dicarbonitrile |
| D | 7-methyl-1,4-dithiino-2(2,3-b)-quinoxaline-2,3-dicarbonitrile |
| E | 1,4-dithiino-(2,3-b)-quinoxaline-2,3-dicarbonitrile |
| F | 7-nitro-8-methyl-1,4-dithiino-(2,3-b)-quinoxaline-2,3-dicarbonitrile |
| G | 7-chloro-8-nitro-1,4-dithiino-(2,3-b)-quinoxaline-2,3-dicarbonitrile |
| H | 7-cyano-1,4-dithiino-(2,3-b)-quinoxaline-2,3-dicarbonitrile |
| I | 7-carbomethoxy-1,4-dithiino-(2,3-b)-quinoxaline-2,3-dicarbonitrile |
| J | 7-methoxy-1,4-dithiino-(2,3-b)-quinoxaline-2,3-dicarbonitrile |
| K | 7-trifluoromethyl-1,4-dithiino-(2,3-b)-quinoxaline-2,3-dicarbonitrile |
| L | 6-nitro-1,3-dithiolo-(4,5-b)-quinoxaline-2-ylidene-propanedinitrile |
| M | 6,7-dinitro-1,3-dithiolo-(4,5-b)-quinoxaline-2-ylidene-propanedinitrile |
| N | 6-methyl-1,3-dithiolo-(4,5-b)-quinoxaline-2-ylidene-propanedinitrile |
| O | 6-chloro-1,3-dithiolo-(4,5-b)-quinoxaline-2-ylidene-propanedinitrile |
| P | 1,3-dithiolo-(4,5-b)-quinoxaline-2-ylidene-propanedinitrile |
| Q | 6-chloro-7-nitro-1,3-dithiolo-(4,5-b)-quinoxaline-2-ylidene-propanedinitrile |
| R | 6-nitro-7-methyl-1,3-dithiolo-(4,5-b)-quinoxaline-2-ylidene-propanedinitrile |
| S | 6-cyano-1,3-dithiolo-(4,5-b)-quinoxaline-2-ylidene-propanedinitrile |
| T | 6-trifluoromethyl-1,3-dithiolo-(4,5-b)-quinoxaline-2-ylidene-propanedinitrile |
| U | 6-methoxy-1,3-dithiolo-(4,5-b)-quinoxaline |
| V | 7-benzoyl-1,4-dithiino-(2,3-b)-quinoxaline-2,3-dicarbonitrile |
| W | 6-benzoyl-1,3-dithiolo-(4,5-b)-quinoxaline-2-ylidene-propanedinitrile |

The antimicrobial activity of the compounds of the present invention is demonstrated by the following techniques.

The minimum inhibitory concentration (MIC) for the compounds listed in Table I is determined for 9 bacteria, using nutrient agar: and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]-glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC test described above along with their respective American Type Culture Collection (ATCC) identification numbers.

TABLE II

Organisms used in the Minimum Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables III and IV, the MIC values of the compounds described in Table I as compared to the MIC of a standard commercial preservatives (with 1-(3-chloroallyl)-3,5,7-triaza-1-azoniaadamantane chloride as the active agent and referred to herein as "STANDARD I") are st forth in the nine bacteria organisms and six yeast/fungi organisms which are listed in Table II.

TABLE III

Minimum Inhibitory Concentrations for Test Compounds in Bacteria Species (in ppm)

| Compound | Bs | Ea | Ec | Kp | Pv | PRD | Pa | Sc | Sa |
|---|---|---|---|---|---|---|---|---|---|
| STANDARD I | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| (A) pH 6.8 | <10 | 100 | 25 | 25 | 50 | 250 | 100 | 50 | <10 |
| pH 8.2 | 100 | >500 | >500 | 500 | >500 | >500 | >500 | >500 | 100 |
| (B) pH 6.8 | 500 | >500 | 250 | 250 | >500 | >500 | >500 | 500 | <10 |
| pH 8.2 | 25 | >500 | >500 | >500 | >500 | >500 | >500 | >500 | <10 |
| (C) pH 6.8 | 25 | >500 | >500 | >500 | >500 | >500 | >500 | >500 | 50 |
| pH 8.2 | 25 | >500 | >500 | >500 | >500 | >500 | >500 | >500 | 50 |
| (D) pH 6.8 | 25 | >500 | >500 | >500 | >500 | >500 | >500 | >500 | 100 |
| pH 8.2 | 250 | >500 | >500 | >500 | >500 | >500 | >500 | >500 | 500 |
| (E) pH 6.8 | 50 | >500 | >500 | 500 | >500 | >500 | >500 | >500 | 25 |
| pH 8.2 | >500 | >500 | >500 | >500 | >500 | >500 | >500 | >500 | <10 |
| (F) pH 6.8 | <10 | 500 | 250 | 100 | 50 | >500 | 500 | 250 | <10 |
| pH 8.2 | 50 | >500 | >500 | >500 | >500 | >500 | >500 | >500 | 50 |
| (G) pH 6.8 | 250 | >500 | >500 | 500 | >500 | >500 | >500 | >500 | 25 |
| pH 8.2 | 100 | >500 | >500 | >500 | >500 | >500 | >500 | >500 | 50 |
| (H) pH 6.8 | <10 | >500 | >500 | 500 | 500 | >500 | >500 | >500 | 25 |
| pH 8.2 | 50 | >500 | >500 | >500 | >500 | >500 | >500 | >500 | 50 |
| (I) pH 6.8 | <10 | >500 | 100 | 50 | 100 | 500 | >500 | 100 | 25 |
| pH 8.2 | 50 | >500 | >500 | >500 | >500 | >500 | >500 | >500 | 100 |
| (J) pH 6.8 | <10 | >500 | >500 | >500 | >500 | >500 | >500 | >500 | <10 |
| pH 8.2 | 25 | >500 | >500 | >500 | >500 | >500 | >500 | >500 | 25 |
| (K) pH 6.8 | <10 | 250 | 50 | 50 | 50 | 250 | 250 | 50 | 25 |
| pH 8.2 | 100 | >500 | >500 | >500 | >500 | >500 | >500 | >500 | 100 |
| (L) pH 6.8 | 100 | >500 | >500 | >500 | >500 | >500 | >500 | >500 | 100 |
| pH 8.2 | >500 | >500 | >500 | >500 | >500 | >500 | >500 | >500 | >500 |
| (M) pH 6.8 | 100 | >500 | >500 | 50 | >500 | >500 | 500 | 500 | <10 |
| pH 8.2 | 250 | >500 | >500 | >500 | >500 | >500 | >500 | >500 | 100 |
| (N) pH 6.8 | >500 | >500 | >500 | >500 | >500 | >500 | >500 | 500 | >500 |
| pH 8.2 | >500 | >500 | >500 | >500 | >500 | >500 | >500 | >500 | >500 |
| (O) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (P) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (Q) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (R) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (S) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (T) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (U) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (V) pH 6.8 | 50 | >500 | >500 | >500 | >500 | >500 | >500 | >500 | 50 |
| pH 8.2 | >500 | >500 | >500 | >500 | >500 | >500 | >500 | >500 | >500 |

TABLE III-continued

Minimum Inhibitory Concentrations for Test Compounds in Bacteria Species (in ppm)

| | ORGANISMS | | | | | | | | |
|---|---|---|---|---|---|---|---|---|---|
| Compound | Bs | Ea | Ec | Kp | Pv | PRD | Pa | Sc | Sa |
| (W) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |

TABLE IV

Minimum Inhibitory Concentrations for Test Compounds in Yeast/Fungi Species (in ppm)

| | ORGANISMS | | | | | | |
|---|---|---|---|---|---|---|---|
| COMPOUND | An | Ca | Pc | Sc | Tv | Ap | Fo |
| STANDARD I | >500 | >500 | >500 | >500 | >500 | >500 | >500 |
| A | 2.5 | 2.5 | 2.5 | 2.5 | 10 | 2.5 | 2.5 |
| B | 25 | 25 | 10 | 25 | 50 | 5 | 25 |
| C | 25 | <10 | <10 | <10 | 250 | <10 | 25 |
| D | 50 | 50 | 50 | 25 | 100 | 25 | 50 |
| E | <10 | <10 | <10 | <10 | 100 | <10 | 50 |
| F | <10 | <10 | <10 | <10 | 25 | <10 | <10 |
| G | 25 | 25 | 100 | 25 | 100 | 25 | 100 |
| H | 25 | 25 | <10 | <10 | 100 | <10 | 50 |
| I | <10 | <10 | <10 | <10 | 25 | <10 | <10 |
| J | 25 | 25 | 25 | <10 | 100 | — | 25 |
| K | 25 | <10 | 25 | <10 | 25 | <10 | 25 |
| L | 2.5 | 10 | 2.5 | 5 | 10 | 5 | 10 |
| M | 2.5 | 2.5 | 2.5 | 2.5 | 10 | 2.5 | 5 |
| N | 500 | >500 | 500 | >500 | >500 | 500 | >500 |
| O | 500 | >500 | 500 | >500 | >500 | 500 | >500 |
| P | 500 | >500 | 500 | >500 | >500 | 500 | >500 |
| Q | 500 | 500 | 500 | 500 | >500 | 50 | >500 |
| R | 100 | >500 | 50 | 500 | >500 | 500 | >500 |
| S | 100 | 500 | 100 | 500 | >500 | 100 | 500 |
| T | 250 | >500 | 250 | >500 | >500 | 250 | >500 |
| U | >500 | >500 | >500 | >500 | >500 | — | >500 |
| V | 250 | 500 | 250 | 500 | 500 | 250 | 500 |
| W | >500 | >500 | >500 | >500 | >500 | 500 | >500 |

Marine Antifouling Activity

The present invention is also directed to a method for inhibiting marine organisms. The term "marine organisms" is meant to include marine animals, such as barnacles, serpulid, bryozoa, oysters and hydroids, marine plants, such as green algae and brown algae, and other typical marine life. The method for inhibiting marine organisms comprises contacting a surface exposed to a marine environment in which marine organisms grow with a marine antifouling effective amount of the compound of this invention.

As appreciated in the art, not all of the compounds disclosed herein are active at the same concentrations or against the same marine organism species. That is, there is some compound-to-compound variation in marine antifouling potency and spectrum of marine antifouling activity. Furthermore, a compound's marine antifouling activity may be dependent on the specific materials with which the compound is formulated to form a marine antifouling composition.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment in which marine organisms grow" refers to a surface where a marine organism naturally or normally lives or grows. Typically, such an surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is $0.381 \times 10^{-3}$ m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

A candidate marine antifoulant compound (1.0 g) is stirred into a resinous latex binder (9.0 g). A portion of the compound/binder mixture (1.5 g) is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit for between ten to thirty minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine surfactant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 3 and 6 weeks during which time the control test panels become substantially covered with mature marine organism growth on both the topside and underside exposures.

After being removed from the exposure support apparatus, each test panel is inspected and rated for marine organism growth on both the treated and untreated areas of the test panel. The marine organisms present on the treated and untreated areas are noted. The presence of algea spores and bacterial slime are noted but not included in rating each test panel. The test panels are rated on a scale from 10 (representing completely free of marine organism growth) to 0 (representing completely covered with marine organism growth).

In Table V, the marine antifouling rating values for some of the compounds listed in Table I are set forth, as well as the ratings for control panels and panels using a standard commercial marine antifouling compound (with 5-chloro-2-methyl-4-isothiazolin-3-one and 2-methyl-4-isothiazolin-3-one as the active agents and referred to herein as "STANDARD II").

TABLE V

| Marine Antifouling Rating for Test Compounds | | | | |
|---|---|---|---|---|
| | Marine Antifouling Ratings | | | |
| | 3 Week Test | | 6 Week Test | |
| Compound | Top Panel | Bottom Panel | Top Panel | Bottom Panel |
| A | 9 | 9 | 8 | 3 |
| B | 6 | 3 | 3 | 0 |
| C | 0 | 9 | 5 | 0 |
| D | 4 | 3 | 3 | 0 |
| E | 8 | 4 | 9 | 0 |
| L | 7 | 7 | 9 | 0 |
| M | 9 | 9 | 5 | 1 |
| O | 0 | 2 | 6 | 0 |
| Control | 3 | 6 | 2 | 1 |

TABLE V-continued

| Marine Antifouling Rating for Test Compounds | | | | |
|---|---|---|---|---|
| | Marine Antifouling Ratings | | | |
| | 3 Week Test | | 6 Week Test | |
| Compound | Top Panel | Bottom Panel | Top Panel | Bottom Panel |
| STANDARD II | 1 | 3 | 2 | 0 |

What is claimed is:

1. A compound corresponding to the formula

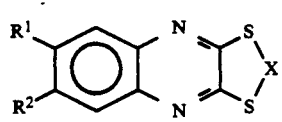

wherein X represents:

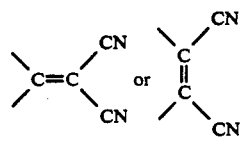

and $R^1$ and $R^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without halogen substituents, provided that at least one of $R^1$ and $R^2$ is a nitro, cyano, alkoxy, alkylcarbonyl, or an alkoxy carbonyl group.

2. The compound of claim 1 wherein $R^1$ and $R^2$ independently represent hydrogen, halogen, nitro, cyano, an alkyl of 1 to 4 carbon atoms, an alkoxy with an alkyl group of 1 to 3 carbon atoms, or an alkoxy carbonyl group with an alkyl group of 1 to 3 carbon atoms.

3. The compound of claim 1 wherein $R^1$ represents CN, $CO_2CH_3$, $OCH_3$, $COC_6H_5$ or $NO_2$ when $R^2$ represents H.

4. The compound of claim 1 wherein $R^1$ represents H, Cl, $CH_3$ and $NO_2$ when $R^2$ represents $NO_2$.

5. An antimicrobial composition comprising an inert diluent and an antimicrobially-effective amount of a compound corresponding to the formula:

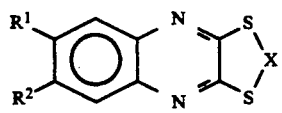

wherein X represents:

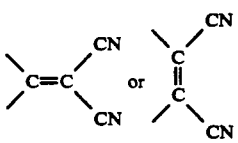

and $R^1$ and $R^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without halogen substituents, provided that at least one of $R^1$ and $R^2$ is a nitro, cyano, alkoxy, alkylcarbonyl, or an alkoxy carbonyl group.

6. The compound of claim 5 wherein $R^1$ and $R^2$ independently represent hydrogen, halogen, nitro, cyano, an alkyl of 1 to 4 carbon atoms, an alkoxy with an alkyl group of 1 to 3 carbon atoms, or an alkoxy carbonyl group with an alkyl group of 1 to 3 carbon atoms.

7. The composition of claim 5 wherein $R^1$ represents CN, $CO_2CH_3$, $OCH_3$, $COC_6H_5$ when $R^2$ represents H.

8. The composition of claim 5 wherein $R^1$ represents H, Cl, $CH_3$ or $NO_2$ when $R^2$ represents $NO_2$.

9. The compound of claim 5 wherein the compound is present in the composition in an amount to provide from about 1 part per million to about 5,000 parts per million by weight of the compound to an antimicrobial habitat that is contacted with the composition.

10. A method for inhibiting microorganisms in a microbial habitat comprising contacting said microbial habitat with an antimicrobially-effective amount of a compound corresponding to the formula:

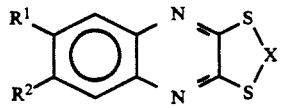

wherein X represents:

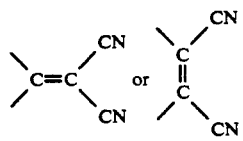

and $R^1$ and $R^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without halogen substituents, provided that at least one of $R^1$ and $R^2$ is a nitro, cyano, alkoxy, alkylcarbonyl, or an alkoxy carbonyl group.

11. The method of claim 10 wherein $R^1$ and $R^2$ independently represent hydrogen, halogen, nitro, cyano, an alkyl of 1 to 4 carbon atoms, an alkoxy with an alkyl group of 1 to 3 carbon atoms, or an alkoxy carbonyl group with an alkyl group of 1 to 3 carbon atoms.

12. The method of claim 10 wherein $R^1$ represents CN, $CO_2CH_3$, $OCH_3$, $COC_6H_5$ or $NO_2$ when $R^2$ represents H.

13. The method of claim 10 wherein $R^1$ represents H, Cl, $CH_3$ or $NO_2$ when $R^2$ represents $NO_2$.

14. The method of claim 10 wherein the compound is used in an amount to provide from about 1 part per million to about 5,000 parts per million by weight of the compound to a microbial habitat being contacted with the composition.

15. A composition useful in preventing the growth of marine organisms on a surface exposed to a marine environment in which marine organisms grow comprising an inert diluent and a marine antifouling effective amount of a compound corresponding to the formula:

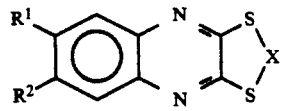

wherein X represents:

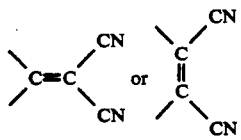

and $R^1$ and $R^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without halogen substituents, provided that at least one of $R^1$ and $R^2$ is a nitro, cyano, alkoxy, alkylcarbonyl, or an alkoxy carbonyl group.

16. The composition of claim 15 wherein $R^1$ and $R^2$ independently represent hydrogen, halogen, nitro, cyano, an alkyl of 1 to 4 carbon atoms, an alkoxy with an alkyl group of 1 to 3 carbon atoms, or an alkoxy carbonyl group with an alkyl group of 1 to 3 carbon atoms.

17. The composition of claim 15 wherein $R^1$ represents F, Cl, $CH_3$, $CF_3$, CN, $CO_2CH_3$, $OCH_3$, $COC_6H_5$ or $NO_2$ when $R^2$ represents H.

18. The composition of claim 15 wherein $R^1$ represents H, Cl, $CH_3$ or $NO_2$ when $R^2$ represents $NO_2$.

19. The composition of claim 15 wherein the compound is present in the compositions in an amount from about 1 weight percent to about 30 weight percent.

20. A method for preventing the growth of marine organisms on a surface exposed to a marine environment in which marine organisms grow comprising contacting said surface with a marine antifouling effective amount of a compound corresponding to the formula:

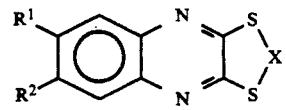

wherein X represents:

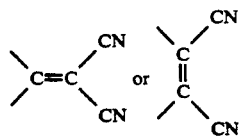

and $R^1$ and $R^2$ independently represent hydrogen, halogen, nitro, cyano, alkyl, alkoxy, arylcarbonyl, or an alkoxy carbonyl group, wherein the alkyl, alkoxy, arylcarbonyl, or alkoxy carbonyl may be with or without halogen substituents.

21. The composition of claim 20 wherein $R^1$ and $R^2$ independently represent hydrogen, halogen, nitro, cyano, an alkyl of 1 to 4 carbon atoms, an alkoxy with an alkyl group of 1 to 3 carbon atoms, or an alkoxy carbonyl group with an alkyl group of 1 to 3 carbon atoms.

22. The composition of claim 20 wherein $R^1$ represents F, Cl, $CH_3$, $CF_3$, CN, $CO_2CH_3$, $OCH_3$, $COC_6H_5$ or $NO_2$ when $R^2$ represents H.

23. The composition of claim 20 wherein $R^1$ represents H, Cl, $CH_3$ or $NO_2$ when $R^2$ represents $NO_2$.

24. The method of claim 20 wherein the compound is contacted with the surface in an amount from about 1 weight percent to about 30 weight percent of a composition comprising an inert diluent and the compound.

* * * * *

UNITED STATES PATENT AND TRADEMARK OFFICE
CERTIFICATE OF CORRECTION

PATENT NO. : 5,200,409

DATED : April 6, 1993

INVENTOR(S) : Duane R. Romer et al.

It is certified that error appears in the above-identified patent and that said Letters Patent is hereby corrected as shown below:

Column 21, line 13, "The compound of claim 5" should read --the composition of claim 5--.

Column 22, line 31, "compositions" should read --composition--.

Column 22, line 56, "The composition" should read --The method--.

Column 22, line 60, "The composition" should read --The method--.

Column 22, line 61, "$COC_6H_5$" should be deleted.

Column 22, line 63, "The composition" should read -- The method--.

Signed and Sealed this

Twenty-sixth Day of April, 1994

Attest:

BRUCE LEHMAN

Attesting Officer     Commissioner of Patents and Trademarks